United States Patent [19]

Zagata et al.

[11] 4,075,232

[45] Feb. 21, 1978

[54] PREPARATION OF MALEIC ANHYDRIDE FROM N-BUTENE IN A ONE-REACTOR, FLUID-BED SYSTEM USING TWO DIFFERENT CATALYSTS

[75] Inventors: Robert J. Zagata, Seven Hills; Ernest C. Milberger, Solon, both of Ohio

[73] Assignee: The Standard Oil Company, Cleveland, Ohio

[21] Appl. No.: 556,092

[22] Filed: Mar. 6, 1975

[51] Int. Cl.$^2$ ............................................ C07D 307/60
[52] U.S. Cl. ............................ 260/346.75; 260/687 R
[58] Field of Search ......................... 260/346.8, 680 E

[56] References Cited

U.S. PATENT DOCUMENTS

| 3,110,746 | 11/1963 | Voge et al. | 260/680 E |
| 3,919,257 | 11/1975 | Milberger et al. | 260/346.8 A |

FOREIGN PATENT DOCUMENTS 7,300,685   1/1973   Japan ................................ 260/346.8

OTHER PUBLICATIONS

Ai et al., Bulletin of the Chem. Soc. of Japan, vol. 44, pp. 3081–3085 (1971).

Primary Examiner—Henry R. Jiles
Assistant Examiner—Bernard Dentz
Attorney, Agent, or Firm—Evelyn R. Kosman; Herbert D. Knudsen; Larry W. Evans

[57] ABSTRACT

Maleic anhydride is prepared by reacting n-butene with molecular oxygen at a temperature of about 200° to about 600° C in a fluid-bed reactor using a catalyst charge containing two different catalysts--the first catalyst being one that is especially effective for preparing butadiene from the n-butylenes; and the second catalyst being one that is especially effective for preparing maleic anhydride from butadiene. Unexpectedly, substantial yields of maleic anhydride are obtained.

10 Claims, No Drawings

PREPARATION OF MALEIC ANHYDRIDE FROM N-BUTENE IN A ONE-REACTOR, FLUID-BED SYSTEM USING TWO DIFFERENT CATALYSTS

BACKGROUND OF THE INVENTION

The oxidation of n-butene to maleic anhydride has been conducted in two fixed-bed reactors containing two different catalysts for the best yields. Combining the two catalysts into one reactor has not been considered to be advisable, because the second catalyst attacks the olefin in such a manner that by-products are formed. Thus, before the desired reaction could occur, undesirable by-products, rather than the desired maleic anhydride, are formed.

Various catalysts that are effective for the conversion of n-butene are well known. Representative patents that exemplify such catalysts include: U.S. Pat. Nos. 3,414,631 and 3,642,930.

The second catalysts that are used in the invention are also known. Catalysts that are representative of the second catalyst of the invention are represented by U.S. Pat. applications Ser. No. 177,105, filed Sept. 1, 1971 now U.S. Pat. No. 3,907,834; Ser. No. 250,660, filed May 5, 1972 now abandoned; and Japanese Patent No. 25,736/71.

The combination of two catalysts into one reactor in a fluid-bed oxidation of the olefin to the anhydride, however, is not known. Also, the substantial yields of maleic anhydride obtained by the present invention could not be expected from the art.

SUMMARY OF THE INVENTION

It has now been discovered according to the present invention that the preparation of maleic anhydride by the reaction of n-butene with molecular oxygen in the presence of an oxidation catalyst is improved by (a) conducting the reaction in a fluid-bed reactor wherein the oxidation catalyst is maintained in one, substantially undivided reaction zone in such a manner that the oxidation catalyst can move to any point in the reaction zone, and (b) using as the oxidation catalyst a catalyst containing two different catalysts—the first catalyst being one that is especially effective for the oxidation of n-butene to butadiene; and the second catalyst being one that is especially effective for the oxidation of butadiene to maleic anhydride. Surprisingly, use of the process of the invention results in substantial per pass conversions to useful products while the capital cost of two separate reactor systems employed in the art is avoided.

As noted above, the present invention is a process for preparing maleic anhydride from n-butene using process conditions, reactant feeds and reaction parameters within the ranges described in the art. The novelty of the present invention resides in the use of a fluid-bed reactor using an oxidation catalyst containing two different catalysts.

One of the most surprising aspect of the present invention is that two different reactions can be compatibly run at a single reaction zone to obtain substantial yields of the desired products. It would be expected that one of the two reactions would dominate, and that a poor yield of maleic anhydride would be obtained.

In addition to the important economic advantage associated with the use of a single reactor, other outstanding advantages include the avoidance of the explosion hazard which is of some concern in the fixed-bed reactor as a result of combining hydrocarbon and air in proportions within the explosive range prior to the reaction. In the present process, the hydrocarbon and air can be mixed in the presence of the fluidized catalyst bed to avoid the explosion hazard. Further, there is the important advantage in the present process of dissipating heat generated by the exothermic reaction, also a problem characteristically associated with the fixed-bed catalytic processes.

Fluid-bed reactors suitable for use in the present invention are well known. Broadly, these reactors contain a fine particle bed of the oxidation catalyst which is expanded by the flow of reactants through the catalyst. In the preferred practice of the invention, the oxidation catalyst in the fluid-bed reactor has a particle size of less than about 300 microns; and during operation of the reactor, the volume of the bed of oxidation catalyst is about 5 to about 50% greater than the volume of the unexpanded bed.

The fluid-bed reactor may have essentially any design that is compatible with the process of the invention. One basic criterion is that there is one, substantially undivided reaction zones formed by the fluid-bed reactor. In the reaction zone, the reactants form the desired products in the presence of the oxidation catalyst. One important aspect of this reaction zone is that the oxidation catalyst of the invention can move throughout the reaction zone. Of course, in the actual design of a fluid-bed reactor there are areas where movement of the oxidation catalyst is substantially greater than the movement in other areas; therefore, the limitation of the invention should not be read to demand equal movement of all catalyst particles throughout the bed. Instead, this limitation implies that the particles of the oxidation catalyst in the normal operation of the fluid-bed reactor are capable of moving to any point in the reaction zone.

The fluid-bed reactor of the invention may be an open-bed reactor where there is little or no restriction to the flow of the oxidation catalyst, or the fluid-bed reactor could be constructed having sieve trays, such as those described in U.S. Pat. No. 3,230,246 for improving the contact of the reactants with the catalyst while at the same time allowing relatively free movement of the oxidation catalyst throughout the reaction zone. In addition to the possible use of sieve trays, most reactors would use cooling coils in the reactor where a heat transfer fluid is indirectly contacted with the hot gases generated in the exothermic reaction. All of these reactor modifications provide a substantially undivided reaction zone as is required by the present invention.

The second major aspect of the present invention is the particular oxidation catalyst employed. As noted, there are not one but two different catalysts. The first catalyst may be any catalyst that is capable of oxidatively dehydrogenating n-butene, that is n-butene-1 or n-butene-2 or their mixtures, to butadiene. Catalysts capable of accomplishing this function are widely known, see for example the patents cited in the Background of the Invention. Any such catalyst may be used as the first catalyst in the oxidation catalyst of the present invention. Similarly, any catalyst that can convert n-aliphatic hydrocarbons of four carbons to maleic anhydride can be used as the second catalyst. This catalyst preferably is an acidic catalyst which oxidizes butadiene to maleic anhydride.

These catalysts are oxides in the oxidation state designated by the surroundings. By the term "oxides" is meant oxides, mixed oxides, oxide complexes, solid-state solutions and other such structures, wherein oxygen is incorporated into the catalytic structure. These catalysts during the process of the invention would always contain more oxygens than the sum of their subscripts.

Preferred catalysts which are used for the first catalyst are those that contain at least an oxide of molybdenum. Of these catalysts, those containing at least the oxides of bismuth and molybdenum are preferred, with those of the following formula being especially preferred:

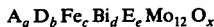
$$A_a D_b Fe_c Bi_d E_e Mo_{12} O_x$$

wherein A is an alkali metal, alkaline earth metal, rare earth metal, Nb, Ta, Tl or mixture thereof;
D is Ni, Co or mixture thereof;
E is P, As, Sb or mixture thereof; and wherein
  $a$ is 0 to about 8;
  $b$ is 0 to about 20;
  $c$ and $d$ are 0.1 to about 10;
  $e$ is 0 to about 3; and
  $x$ is a number required to satisfy the valence requirements of the other elements present.

These catalysts have been found to be extremely effective in oxydehydrogenation.

For use as the second catalyst that converts the hydrocarbons to maleic anhydride, preferred catalysts have the formula:

$$A_a V_b Fe_c Sb_d Mo_e O_x$$

wherein A is a metal oxide, Te, P, As or mixture thereof; and wherein
  $a$ is 0 to about 3;
  $b$ and $c$ are 0 to 6;
  $d$ is 0 to about 12;
  $e$ is 0.1 to about 12; and
  $x$ is the number of oxygens to satisfy the valence requirements of the other elements present.

Preferred are those catalysts wherein A is Al, Cr, Co, Ni, Cu, Bi, Te, B, P, W or mixture thereof. Most preferred are catalysts containing molybdenum in combination with vanadium, tungsten or antimony, i.e., in the formula where A is tungsten and $a$ and $b$ are positive numbers or where $d$ is a positive number. These catalysts are especially effective in the preparation of maleic anhydride. Representative examples of these catalysts that are known are also shown in the Background of the Invention. These catalysts are also oxides that contain a number of oxygens dictated by their surroundings. Both of the catalysts used in the present invention are conveniently prepared by techniques that are shown in the prior art.

The two catalysts which comprise the oxidation catalyst employed in the present invention are those that are shown in the art. Although the particular method of preparation is important to catalytic activity, these methods are shown in the art, and specific methods of preparing certain catalysts are shown in the examples.

As discussed above, the oxidation catalyst of the invention contains two different catalysts. In a preferred practice of the present invention, the oxidation catalyst comprises a physical mixture of separate particles of the first catalyst and separate particles of the second catalyst. Other techniques for bringing the different catalysts into a single fluid-bed reactor are easily conceived. For example, the catalyst charge of the invention could comprise particles containing a mixture of the two catalysts.

Another important aspect of the oxidation catalyst is the relative proportion of the two different catalysts. Although the two catalysts can be mixed in any proportion, normally at least about 5 percent by weight of both catalysts is present in the reactor. The exact optimum ratio depends upon the specific catalysts and reaction conditions employed. In the preferred practice of the invention, it has been found that higher conversion of the reactants to the anhydride can be obtained by starting with a catalyst mixture containing a greater proportion of the oxydehydrogenation catalyst. To determine the optimum production of maleic anhydride, for example, a catalyst mixture containing more than 95% by weight of the first catalyst which is used to oxydehydrogenate the olefin to butadiene can be run under a given set of conditions, and portions of the second catalyst (the catalyst that converts butadiene to maleic anhydride) are added until a desirable low (less than 5%) concentration of butadiene is obtained. Alternatively, a relatively high concentration of butadiene can be recovered in the reactor effluent for use per se for use as recycle feed to the fluid-bed reactor.

In the preferred practice of the invention, about 5 to about 40% by weight of the active ingredients of the oxidation catalyst is the second catalyst, with about 10 to about 30% by weight being more preferred. These concentrations give small yields of undesirable by-products.

Although the oxidation catalyst of the invention usually contains only two catalyts, it is also contemplated by the invention that more than two catalysts could be used by selecting more than one catalyst from either or both of the groups of catalysts or by employing another catalyst that does not deleteriously affect the reaction of the present invention. Also, in addition to the active catalysts, it is technically feasible to add to the oxidation catalyst a solid particulate diluent to improve fluidization, to act as a force to moderate the heat of the reaction or for some other purpose.

As noted above, the process conditions, reactant ratios and reaction parameters employed in the present invention are substantially the same as the art. The temperature of the reaction generally ranges between about 200° and about 600° C, with temperatures of about 300° to about 450° C being preferred. Atmospheric, subatmospheric or superatmospheric pressures may be conveniently employed.

While the ratio of molecular oxygen may vary within broad limits, the molar ratio of molecular oxygen to olefin is normally about 4 to about 12. In terms of air, this would means that about 20 to about 60 volumes of air are employed per volume of olefin. In addition to the reactants, inert diluent gases such as steam, nitrogen and carbon dioxide could be conveniently included in the feed to improve the temperature control and increase the selectivity to the anhydride.

The other aspects of the process of the invention are not critical. Specific procedures for conducting the reaction are shown in the Specific Embodiments. The important factor of the invention is the discovery that use of two different catalysts mixed in a fluid-bed reactor give surprisingly high yields of maleic anhydride.

SPECIFIC EXAMPLES

Comparative Example A and Examples 1–5

Comparison of mixed catalyst with second catalyst only.

Maleic anhydride was prepared from butene-2 in a fluid bed reactor using a mixture of a first and second state catalyst as compared with the second stage catalyst alone. The catalysts for this comparison were prepared as follows:

First catalyst — 50% $K_{0.1}Ni_{2.5}Co_{4.5}Fe_3BiP_{0.5}Mo_{12}O_x$ + 50% $SiO_2$ A solution of 127.1 g. ammonium heptamolybdate $(NH_4)_6Mo_7O_{24}\cdot 4H_2O$ and water was prepared. To this solution was added 6.9 g. of a 42.5% solution of $H_3PO_4$ and 256 g. of Nalco 40% silica sol to form a slurry. Separately, an aqueous solution containing 72.7 g., ferric nitrate, $Fe(NO_3)_3\cdot 9H_2O$; 29.1 g. bismuth nitrate, $Bi(NO_3)_3\cdot 5H_2O$; 78.6 g. cobalt nitrate, $Co(NO_3)_2\cdot 6H_2O$; 43.6 g. nickel nitrate $Ni(NO_3)_2\cdot 6H_2O$; and 6.1 g. of a 10% potassium nitrate solution was prepared. The solution of metal nitrates was slowly added to the slurry. The resulting slurry was spray dried, and the solid obtained was heat treated at 290° C for three hours, at 425° C for 3 hours and at 550° C for 16 hours. The solid catalyst had a surface area of 25.1 m²/g. and a particle size range of about 30 to 80 microns.

Second Catalyst

80% $SbMo_3V_{0.1}Fe_{0.2}O_x + W°_{0.06}$ + 20% $SiO_2$ 24.06 Kg. $MoO_3$, 505.5 gms. $V_2O_5$, 894 gms. $Fe_2O_3$, and 617 gms. tungsten metal powder were slurried in 77.18 kg. water, and the slurry was stirred and heated to the boiling point. Refluxing was continued for two additional hours. At this point 25.04 kg. of a silica sol containing 34% silica was added with stirring. Finally 8.13 kg. $Sb_2O_3$ was added and the slurry was refluxed for an additional hour, then the slurry was concentrated by distilling off 31.8 kg. water. The remaining slurry was then spray dried to yield a microspheroidal product in the size range from about 30 to 105 microns.

A fluid bed reactor was constructed from a 3.8 cm. inside diameter stainless steel tube having an inlet for the air at the bottom, a separate sparger for the hydrocarbon feed situated above the air inlet, and an exit for products at the top. On the inside of the reactor and spaced along the length of the reactor were 12 sieve trays. The sieve trays were constructed and installed in such a manner that the catalyst particles were able to move throughout the reaction zone. A reactor feed of butene-2 (consisting of a mixture of 47% cis and 53% trans isomers) was fed to the reactor in a molar ratio of air to butene-2 of 20 at an apparent contact time shown in Table I. The products were analyzed by titration, and the results of these tests comparing a 50–50 weight percent mixed catalyst to a second catalyst alone are shown in Table I, using the following definitions:

$$\% \text{ Single Pass Yield} = \frac{\text{Moles of product} \times 100}{\text{Moles of butene-2 feed}}$$

$$\% \text{ Selectivity} = \frac{\text{Moles of product} \times 100}{\text{Moles of butene-2 reacted}}$$

Table I

| | | Reaction Conditions | | Results, % | | |
|---|---|---|---|---|---|---|
| | | | | Single Pass Maleic | Yield to | Selectivity to useful |
| Example | Catalyst | Temp., °C | C.T.(sec.) | Anhydride | Butadiene | Products |
| Comp. A | Second catalyst only | 391 | 3.0 | 23.0 | 2.9 | 32.0 |
| 1 | Mixed | 371 | 3.1 | 24.0 | 22.6 | 56.8 |
| 2 | Mixed* | 367 | 3.2 | 24.6 | 11.4 | 40.2 |
| 3 | Mixed* | 349 | 3.3 | 18.4 | 23.9 | 54.9 |
| 4 | Mixed** | 374 | 3.6 | 26.5 | 7.1 | 40.8 |
| 5 | Mixed** | 393 | 3.5 | 27.0 | 5.3 | 37.9 |

*Air/H.C. molar ratio = 40.
**First catalyst calcined at 700° C for two additional hours.

EXAMPLES 6–8

Mixed Catalyst with Different Second Catalyst.

A different second catalyst was prepared as follows:

Second Catalyst — 62% $W_{1.2}V_3Mo_{12}O_x$ + 38% $SiO_2$

Water was heated in a stainless steel container to a temperature of 75° C. To the water was added 3923 g. of $(NH_4)_6Mo_7O_{24}\cdot 4H_2O$, 606 g. of $(NH_4)_6W_7O_{24}\cdot 6H_2O$ and 650 g. of $NH_4VO_3$ and 7604 g. of silica. The mixture was spray dried and heated to 400° C for 4 hours, and screened to give a particle size of about 30 to 105 microns.

The butene-2 was fed to the reactor under the reaction conditions indicated in Table 2. The same type of fluid reactor was employed in these examples as in Examples 1 to 5 with the exception that the reactor did not contain the sieve trays. The results of these experiments employing a catalyst mixture containing an 80-20 weight ratio of the first catalyst to the second catalyst, respectively, wherein the second catalyst had the composition described above, are summarized in Table 2.

Table 2

| | Reaction Conditions | | | Results, % | | |
|---|---|---|---|---|---|---|
| | | | | Single Pass Yield to | | Selectivity |
| | | | Air/H.C. | Maleic | | to Useful |
| Example | Temp., °C | C.T.(sec.) | Ratio-Molar | Anhydride | Butadiene | Products |
| 6 | 363 | 8.9 | 20 | 29.1 | 10.4 | 39.5 |
| 7 | 371 | 9.1 | 25 | 35.7 | 0.4 | 36.1 |

Table 2-continued

Production of Maleic Anhydride from Butene-2 Using 80-20 Mixture of Different Catalysts in Fluid Bed Reactor

| | Reaction Conditions | | | Results, % | | |
|---|---|---|---|---|---|---|
| | | | | Single Pass Yield to | | Selectivity |
| Example | Temp., °C | C.T.(sec.) | Air/H.C. Ratio-Molar | Maleic Anhydride | Butadiene | to Useful Products |
| 8* | 368 | 8.9 | 25 | 39.9 | 0 | 39.9 |

*Water added to the feed in a molar ratio of $H_2O/H.C.$ of 6.

We claim:

1. In the process for the preparation of maleic anhydride by the reaction of n-butene with molecular oxygen wherein the reaction is carried out in the temperature range of about 200° to 600° C in the presence of an oxidation catalyst, utilizing a molar ratio of molecular oxygen to n-butene in the range of 4 to 12, the improvement comprising:
   a. conducting the reaction in a fluid-bed reactor wherein the oxidation catalyst is maintained in one, substantially undivided reaction zone in such a manner that the oxidation catalyst can move to any point in the reaction zone; and
   b. using as the oxidation catalyst a catalyst comprising a physical mixture of separate particles of first catalyst and separate particles of second catalyst— the first catalyst being one that is especially effective for the oxidation of n-butene to butadiene said first catalyst containing the oxides of at least molybdenum and bismuth, and the second catalyst being one that is especially effective for the oxidation of butadiene to maleic anhydride, said second catalyst containing molybdenum oxide and at least one other metal oxide selected from the group consisting of tungsten, antimony and vanadium.

2. The process in claim 1 wherein the first catalyst has the formula:

$$A_a D_b Fe_c Bi_d E_e Mo_{12} O_x$$

wherein A is an alkali metal, alkaline earth metal, rare earth metal, Nb, Ta, Tl or mixture thereof;
D is Ni, Co or mixture thereof;
E is P, As, Sb or mixture thereof; and wherein
$a$ is 0 to about 8;
$b$ is 0 to about 20;
$c$ and $d$ are 0.1 to about 10;
$e$ is 0 to about 3; and
$x$ is a number required to satisfy the valence requirements of the other elements present.

3. The process in claim 2 wherein the second catalyst has the formula:

$$A_a V_b Fe_c Sb_d Mo_e O_x$$

wherein A is a metal oxide, Te, P, As or mixture thereof; and wherein
$a$ is 0 to about 3;
$b$ and $c$ are 0 to about 6;
$e$ is 0 to about 12;
$e$ is 0.1 to about 12; and
$x$ is the number of oxygens to satisfy the valence requirements of the other elements present.

4. The process in claim 3 wherein the second catalyst contains at least the oxides of molybdenum and antimony.

5. The process in claim 3 wherein the second catalyst contains at least the oxides of molybdenum and tungsten.

6. The process in claim 3 wherein the second catalyst contains at least the oxides of molybdenum and vanadium.

7. The process of claim 3 wherein A of the second catalyst formula is Al, Cr, Co, Ni, Cu, Bi, Te, B, P, W or mixture thereof.

8. The process in claim 3 wherein n-butene is butene-2.

9. The process in claim 8 wherein the reaction temperature is in the range of 300° to 450° C.

10. The process of claim 9 wherein said first catalyst is $K_{0.1}Ni_{2.5}Co_{4.5}Fe_3Bi_1P_{0.5}Mo_{12}O_x$ and said second catalyst is $V_{0.1}Fe_{0.2}SbMo_3O_x + W°_{0.06}$.

* * * * *